United States Patent [19]

Badmajew

[11] Patent Number: 5,130,132

[45] Date of Patent: Jul. 14, 1992

[54] COMPOSITION AND METHOD FOR TREATING NICOTINE DEPENDENCY

[76] Inventor: Vladimir Badmajew, Lortzingstrasse 19, D-5000 Köln 41, Fed. Rep. of Germany

[21] Appl. No.: 397,436

[22] PCT Filed: Jan. 15, 1988

[86] PCT No.: PCT/EP88/00050

§ 371 Date: Jul. 13, 1989

§ 102(e) Date: Jul. 13, 1989

[87] PCT Pub. No.: WO88/05305

PCT Pub. Date: Jul. 28, 1988

[30] Foreign Application Priority Data

Jan. 15, 1987 [DE] Fed. Rep. of Germany ....... 3700982

[51] Int. Cl.$^5$ ................. A61K 35/78; A24F 47/00
[52] U.S. Cl. .................... 424/195.1; 424/48; 424/408; 424/464; 514/813; 131/270
[58] Field of Search ............. 424/195.1, 48, 464, 424/408; 131/270; 514/813

[56] References Cited

U.S. PATENT DOCUMENTS

| 2,600,700 | 6/1952 | Smith | 167/55 |
| 3,011,944 | 12/1961 | Taizo | 424/195.1 |
| 4,871,540 | 10/1989 | Kojima et al. | 424/195.1 |

FOREIGN PATENT DOCUMENTS

| 2175853 | 10/1973 | France . |
| 2375860 | 9/1978 | France ............... 424/195.1 |
| 1108966 | 4/1968 | United Kingdom . |

OTHER PUBLICATIONS

"Codex Vegetables", Steinmetz, pp. 25, 812, 822 (1957).
"Tobacco Experimental and Clinical Studies", Larson et al. The Williams & Wilkins Co. (1961).

Primary Examiner—Johnnie R. Brown
Assistant Examiner—A. Varma
Attorney, Agent, or Firm—Eckert Seamans Cherin & Mellott

[57] ABSTRACT

An anti-smoking remedy with biochemical effect. The remedy consists of non-toxic plant components including *Radix bupleuri*, *Radix peucedani* and *Rhizoma cimicifugae*. Additional components to the preparation can include *Rhizome phragmiles*, or a mixture of *Pinellia ternata* and either Liguiritiae or *Robinia pseudo acacia*.

9 Claims, No Drawings

COMPOSITION AND METHOD FOR TREATING NICOTINE DEPENDENCY

The invention refers to an anti-smoking remedy with biochemical effect. More and more attention is paid to the disturbances of health associated with or caused by smoking. In the meantime it has also become generally known that non-smokers who inhale the smoke of other people's cigarettes have to fear in the long run an impairment of their health. That is why in the last years various methods of medicines against smoking have been presented which aimed to disgust the smoker with smoking, to motivate him psychologically against smoking, to shift the pleasure of smoking to other physical comforts, etc.

The known chemical and biochemical anti-smoking remedies generally have unwanted side effects. Moreover, their efficacy is not always guaranteed. The intake, particularly the prolonged intake of these remedies requires a firm and constant will which, as known by experience, the patient has in the initial phase but often is not able to maintain after a certain period of withdrawal. Especially when the first withdrawal symptoms and side effects, such as weight gain, occur. It is precisely at this moment that the will-power of most of them fails. At this stage the known biochemical remedies do not sufficiently support the patient who is willing to stop smoking.

The objective which underlies this invention is therefore to avoid the detriments of the known biochemical anti-smoking remedies and to present a biochemical remedy which in a relatively short time, for example a few days (2 to 5 days), disgusts the smoker with smoking to such a degree that he will stick to the treatment also for the following days. Already during first days of intake the preparation shall provoke such a strong aversion to smoking that the person who is willing to stop smoking feels physically unwell, in particular nauseous, if he smokes after intake of the preparation or inhales the smoke of other people's cigarettes. The invention aims at producing a strong anti-nicotine effect. A feeling of incompatibility between tobacco products and the invention-conforming preparation is created.

This objective is achieved by anti-smoking remedy with biochemical effect which consists of the following non-toxic plant components: *Radix Bupleuri, Radix Peucedani, Rhizoma Cimicifugae* and *Tubera Pinelliae*. To these components can be added: *Rhizoma Phragmites* or a mixture of *Pinellia ternata* and Liquiritiae; *Robinia pseudo-acacia* can substitute for Liquiritiae.

These components can be presented in various galenic forms, for example chewing tablets, normal tablets for oral use, infusion, etc. Preference is given to the chewing tablet. In the form of a chewing tablet, the strong bitter taste of the preparation is fully perceived, but it can be modified or altered by appropriate additives (sugar, aromatics, etc.).

Combined, the mentioned components cause an aversion to smoke and smoking, and this already at the moment a cigarette is lighted up. Aversion is also felt when inhaling the smoke of other people's cigarettes. In both situations, active and passive smoking, the intake of the pharmaceutical preparation produces a bitter taste in the mouth which, first of all, spoils the pleasure of smoking. In addition an effect is produced on the central nervous system in form of a defense reaction which is attributed to a change in the sensation of taste in the brain. Moreover, the parasympathetic nervous system is stimulated provoking sickness and nausea. Sickness resp. nausea are intensified due to the fact that less oxygen is absorbed when inhaling smoke. The invention-conforming herb mixture strengthnes nerves and organs. The anti-smoking effect is already felt after a few days, for example after 2 to 5 days.

The plant components used have a strong anti-nicotine effect and provoke nausea and even vomiting when smoking a cigarette or inhaling the smoke of other people's cigarettes. This is due to a taste incompatibility between tobacco products and the active constituents of the plants.

The intake of the invention-conforming pharmaceutical preparation leads to a decrease in weight. This is a very important advantage since with the anti-smoking treatments usually applied an increase in weight is observed already a few days after having stopped smoking due to the withdrawal of nicotine. Owing to its weight reducing properties the invention-conforming preparation counteracts this tendency. On the whole the anti-smoking effect of the invention-conforming pharmaceutical preparation is not of psychological nature but is due to a sensory antagonism (incompatibility) which manifests itself not only on a local sensory level but also centrally.

The preparation also proved effective in spoiling the pleasure of drinking coffee. This effect is above all attributed to the presence of Pinellia ternata. A taste incompatibility with coffee is achieved which manifests itself as a prickling, tingling, stinging and burning sensation in the mouth and throat when drinking coffee after the intake of the preparation. The daily coffee consumption decreased in test persons who took the preparation over a prolonged period. Moreover there are some indications that the preparation may also disgust with taking drugs. Preliminary trials also showed a certain efficacy of the preparation in subjects smoking marihuana, in alcohol abuse, and even in the last stage of cocaine dependence.

*Radix Bupleuri* is the root of *Bupleurum felcatum L.* of the Umbelliferae family. The herb grows in Southern and Middle Europe, Eastern Asia and above all in Japan. Its antipyretic properties are generally accepted. The most important chemical constituents are blupleurumol $C_3H_6O_2$ (0.5%), A-Spinasterol (2%), and Rutin $C_2H_{30}O_{16}$ (2%).

Radix Peucedani is the root of Peucadanum praeruptorum Dunn which also belongs to the Umbelliferas family. It is used in gastric diseases and dermatoses. The root contains among other substances essential oils and bitters, above all nodakenin $C_{20}H_{24}O_9$, sponsterol and nodakenetin $C_{14}H_{14}O_4$.

*Rhizoma Cimicifugae* is the root of *Cimicifuga foetida L.* which belongs to the Ranunculaceae family. The plant grows in North America. Its most important constituents are cimicitin $C_{20}H_{34}O_7$ and cimicifugine.

*Tubera Pinelliae* is the bulb, root or stem of *Pineallia ternata Breitenbach* (*P. tuberiferara; triphyllium* of the Araceae family). The plant grows in Eastern Asia. It contains about 0.003 to 0.13% of essential oils, some alkaloids, fatty oily and stark, for ex. pinelin.

Rhizoma Phragmites are the root and stem of *Phragmites communis L. Triniusj* of the gramineae family, the English word for it is reed. About 77% of silicic acid was found in the ashes. It has a sweetish taste and is used in disorders of the lungs, stomach and liver. Constituents are proteins, fats and carbohydrates.

The root of licorice resp. Glycyrrhiza contains steroid-like hormones, to which is attributed an antiphlogistic effect. The main constituent of the root is the triterpene saponin glycyrrhizic acid which has an intensde sweet taste. It forms with water a gelatine-like mixture on the pharyngeal mucosa a protective layer. It is the root of licorice, *Radix glycyrrhizae*, which gives the medicine its pleasant taste. Essential constituents are Glycyrrhizine (10%), Potassium, *Terpenic saponins* (12%), for example the already mentioned Glycyrrhizic acid, Liquiritin, Isoliquiritin (flavonoids), Asparagine (1 to 2%) and Glycymarin (6%; bitter taste).

For a preferred further development of the invention it is proposed that the plant components are present in the following weight percentages:

(Example 1): 25) of *Radiox Bupleuri*, 20% of *Radix Peucedani*, 25% of *Rhizoma Cimicifugae*, 20% of *Tubera Pinelliae* and 10% of *Rhozoma Phragmites*. The base should be a fully dosed (saturated) aqueous solution of 3 to 5 g of *Radix Bupleuri*, 5 to 10 g of *Radix Peucedani*, 3 to 5 g of *Rhizoma Cimicifugae*, 5 to 10 g of *Tubera Pinelliae* and 15 to 30 g of *Rhizoma Phragmites*.

(Example 2): 30% of *Peucedanum praeruptorum* of the Umbelliferae family, 24% of Gentiana barbata of the Gentianceae family, 12% of *Cimicifuga foetida* of the Ranunculaceae family, 4% of licorice or *Robinia pseudo-accacia* both of the Leguminosae family, 12% of *Bupleurum falcatum* of the Umbelliferae family.

For the manufacture of the preparation the plant components are simply blended. It is possible but not necessary to add special binders. For the manufacture of the chewing tablets gum material is used, for example, chickle polyvinylester or polyethylene, i.e. materials which are also used for the manufacture of chewing gum. Preferably sugar obtained from honey is added. The effect of the medicine is particularly long-lasting when used in the galenic presentation of a chewing tablet; thoroughly masticated, the different active substances are better absorbed and display therefore a greater effect.

An infusion can also be prepared. The preparation is the same as with normal tea. Hot water is poured in a cup upon at least one tablet of the invention-conforming pharmaceutical preparation. The infusion should draw for some minutes and should be drunk hot.

One tablet weights 0.5 g. Normal daily dose: one tablet three times a day with a little water. Heavy smokers should double the dose. The tablets should be taken with the meals, before, during or after the meals.

The treatment should be continued until an effect is perceived, but should not exceed five days. If after five days of intake no effect is felt, i.e. no aversion to smoke and for smoking, treatment should be discontinued for 2 to 3 days and then resumed for another five days.

The anti-smoking effect is attributed to the following chemical constituents of the plants:

*Nodakenin (Peucedanum), Gentioside (Gentiana), Cimiciti (Cimicifuge)*, Saponins and *A-Spinasterol (Bupleurum)*.

I claim:

1. An anti-smoking preparation comprising a non-toxic, pharmaceutically effective amount of *Radix Bupleuri, Radix Peucedani, Rhozoma Cimicifugae*, and *Tubera Pinelliae*.

2. The anti-smoking preparation of claim 1 further comprising a non-toxic pharmaceutically effective amount of *Rhizoma Phragmites*.

3. The anti-smoking preparation of claim 1 further comprising a non-toxic pharmaceutically effective amount of Gentiana barbata (gentian) and Liquiritiae.

4. The anti-smoking preparation of claim 2, wherein the components are present in the preparation in the following relative weight ratio: *Radix Bupleuri* 25%, *Radix Peucedani* 20%, *Rhizoma Cimicifugae* 25%, *Tubera Pinelliae* 20%, and *Rhizoma Phragmites* 10%.

5. An anti-smoking preparation comprising a mixture of components in the following relative weight ratio: *Peucedanum praeruptorum* of the *Umbelliferae* family 30%, *Gentiana barbata* of the Gentianaceae family 24%, *Cimicifuga foetida* of the Ranunculaceae family 12%, Luquiritiae of the Leguminosae family or *Robinia pseudoacacia* of the Leguminosae family 4%, *Bupleurum falcatum* of the Umbelliferae family 12%, and *Pinellia ternata* of the Araceae family 18%.

6. The anti-smoking preparation of claim 1, wherein the components are compressed, dry tablets.

7. The anti-smoking preparation of claim 1, wherein the components are present in a binder comprising a chewing gum base.

8. The anti-smoking preparation of claim 7, wherein the chewing gum base contains chicle.

9. A method of treating nicotine dependency in a patient comprising administering to the patient a non-toxic pharmaceutically effective amount of a mixture comprising *Radix Bupleuri, Rhizoma Cimicifugae* and *Radix Peucedani*.

* * * * *